(12) United States Patent
Postolov et al.

(10) Patent No.: US 10,203,289 B2
(45) Date of Patent: Feb. 12, 2019

(54) INSPECTION SYSTEM AND A METHOD FOR INSPECTING A DICED WAFER

(75) Inventors: Yuri Postolov, Afula (IL); Menachem Regensburger, Shimshit (IL)

(73) Assignee: CAMTEK LTD., Migdal Haemek (IL)

( * ) Notice: Subject to any disclaimer, the term of this patent is extended or adjusted under 35 U.S.C. 154(b) by 3577 days.

(21) Appl. No.: 12/064,355

(22) PCT Filed: Aug. 29, 2006

(86) PCT No.: PCT/IL2006/000996
§ 371 (c)(1),
(2), (4) Date: Sep. 6, 2011

(87) PCT Pub. No.: WO2007/026351
PCT Pub. Date: Mar. 8, 2007

(65) Prior Publication Data
US 2011/0310241 A1 Dec. 22, 2011

Related U.S. Application Data (60) Provisional application No. 60/712,142, filed on Aug. 30, 2005, provisional application No. 60/712,143, filed on Aug. 30, 2005, provisional application No. 60/712,144, filed on Aug. 30, 2005.

(51) Int. Cl.
*G01N 21/95* (2006.01)
*G01N 21/956* (2006.01)
*H01L 21/67* (2006.01)

(52) U.S. Cl.
CPC ....... *G01N 21/9501* (2013.01); *G01N 21/956* (2013.01); *H01L 21/67288* (2013.01)

(58) Field of Classification Search
CPC .............. G01N 21/9501; G01N 21/956; H01L 21/67288
See application file for complete search history.

(56) References Cited

U.S. PATENT DOCUMENTS

2003/0063790 A1* 4/2003 Smilansky ............. G01N 21/94
382/145

* cited by examiner

*Primary Examiner* — Siamak Harandi
(74) *Attorney, Agent, or Firm* — Reches Patents (57) ABSTRACT

An inspection system and a method for inspecting a diced wafer. The method includes: acquiring multiple images of multiple portions of the diced wafer according to a predefined image acquisition scheme; locating multiple unique features within the multiple images; and assigning a die index to each die of the multiple dice and associating between the multiple dice and multiple reference dice in response to locations of the multiple unique features and to at least one expected die dimension.

36 Claims, 10 Drawing Sheets

INSPECTION SYSTEM AND A METHOD FOR INSPECTING A DICED WAFER

RELATED APPLICATIONS

This application claims the priority of U.S. provisional patents Ser. No. 60/712,144, titled "Wafer Mapping and Die Alignment for Post Diced Wafer with Non Linear Distortion of Dice", U.S. provisional patents Ser. No. 60/712,143, titled "Automatic die-model creation and wafer mapping for on-line wafer inspection and random retrieval of die-model data" and U.S. provisional patents Ser. No. 60/712,142, titled "Automatic Visual Inspection of Post Diced Wafer Placed on a Grid", all filed on 30 Aug. 2005.

FIELD OF THE INVENTION

This application relates to methods for inspecting diced wafers and an inspection system.

BACKGROUND OF THE INVENTION

Figure 1:
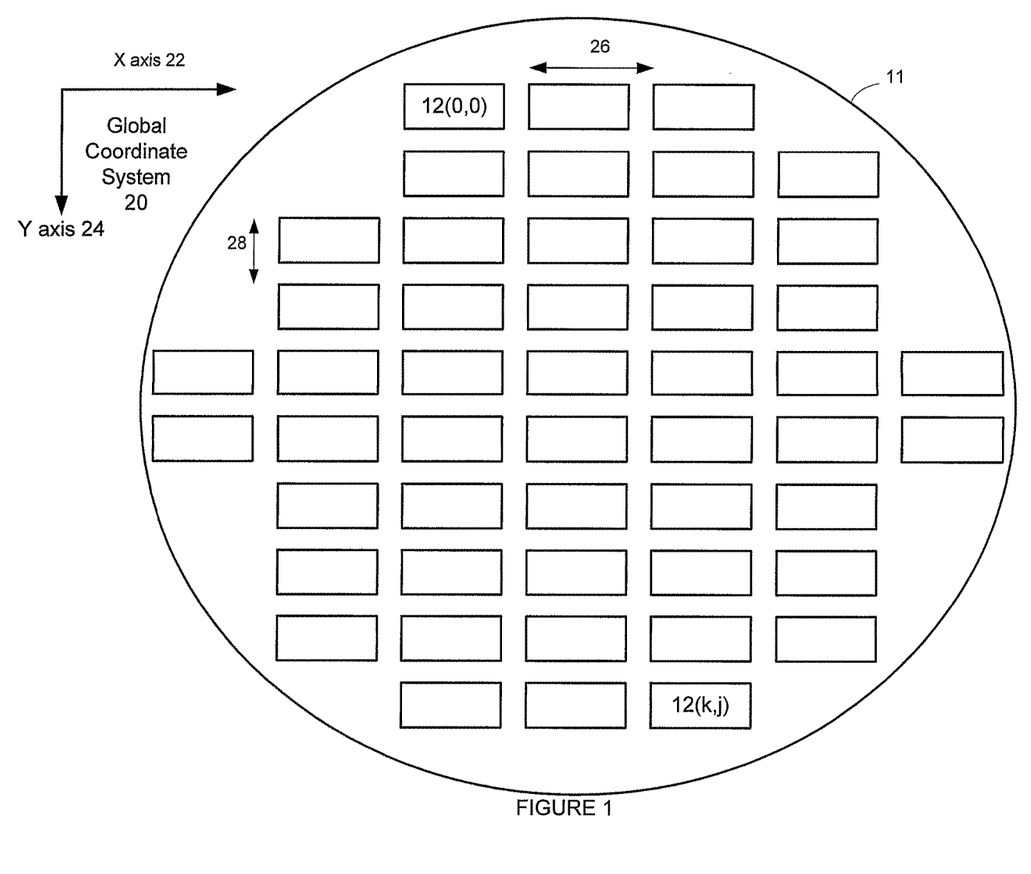
FIG. 1 illustrates a prior art wafer.

Integrated circuits are manufactured by a highly complex and costly manufacturing process. During the first stages of this process a wafer is formed. A wafer includes multiple dice that are arranged in an ordered array of dice wherein the dice are parallel to each other, as illustrated in FIG. 1. Rectangular-shaped dice are arranged in columns and rows and are separated by scribe lines. The dice are characterized by a die X axis pitch 26 and a die Y axis pitch Y 28. Referring to FIG. 1, wafer 11 includes multiple dice 12(0, 0)-12(k,j) that are collectively denoted 12. FIG. 1 also illustrates a global coordinate system 20 that includes X-axis 22 and Y-axis 24. The dice are arranged in parallel to these imaginary axes and are aligned with global coordinate system 20.

Figure 2:
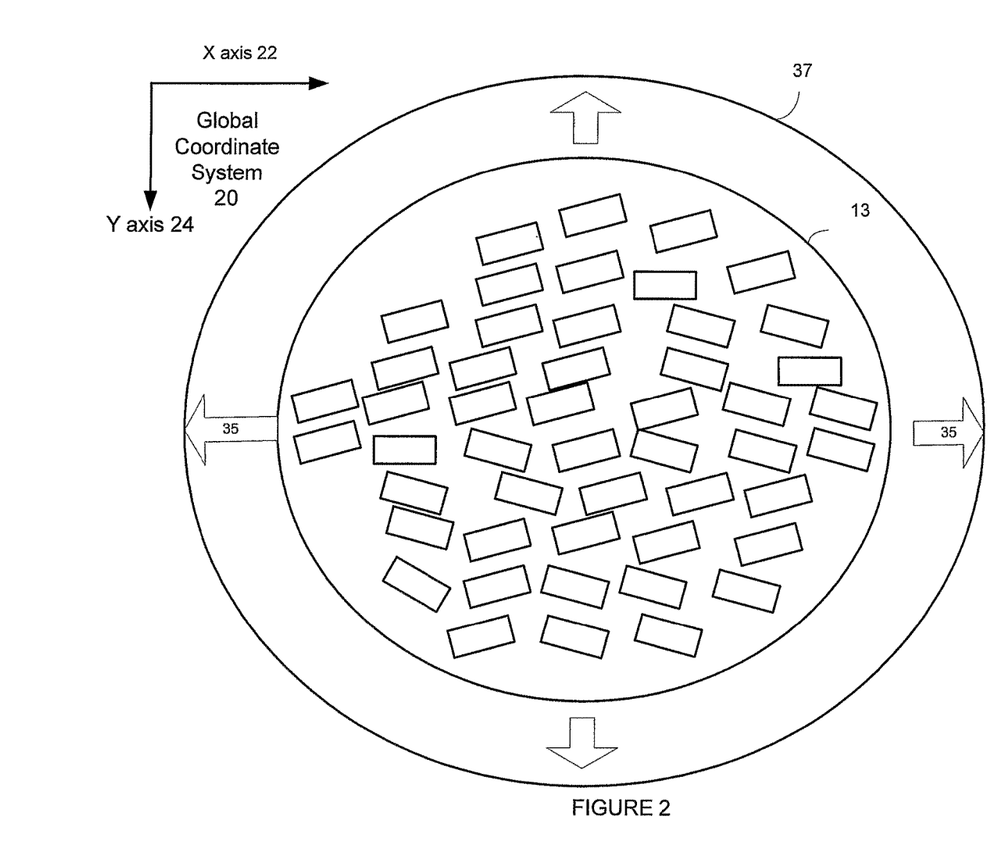
FIG. 2 illustrates a prior art diced wafer and the forces that expand the diced wafer.

During the final manufacturing stages of the wafer the wafer is diced (or sawn) in order to separate between the different dice. The wafer is usually placed on a tape and after the dicing process the dice are then pulled away from each other, conveniently by using an ideally radial force. FIG. 2 illustrates a diced wafer 13, tape 37 and the forces (illustrated by arrows 35) that expand the diced wafer.

The sawing as well as the dice separation process result in a non-linear spatial relationships between the dice of the diced wafer. Each die can be shifted, rotated, sheered and stretched in relation to its previous (pre-dice) position and in relation to adjacent dice.

Figure 3:
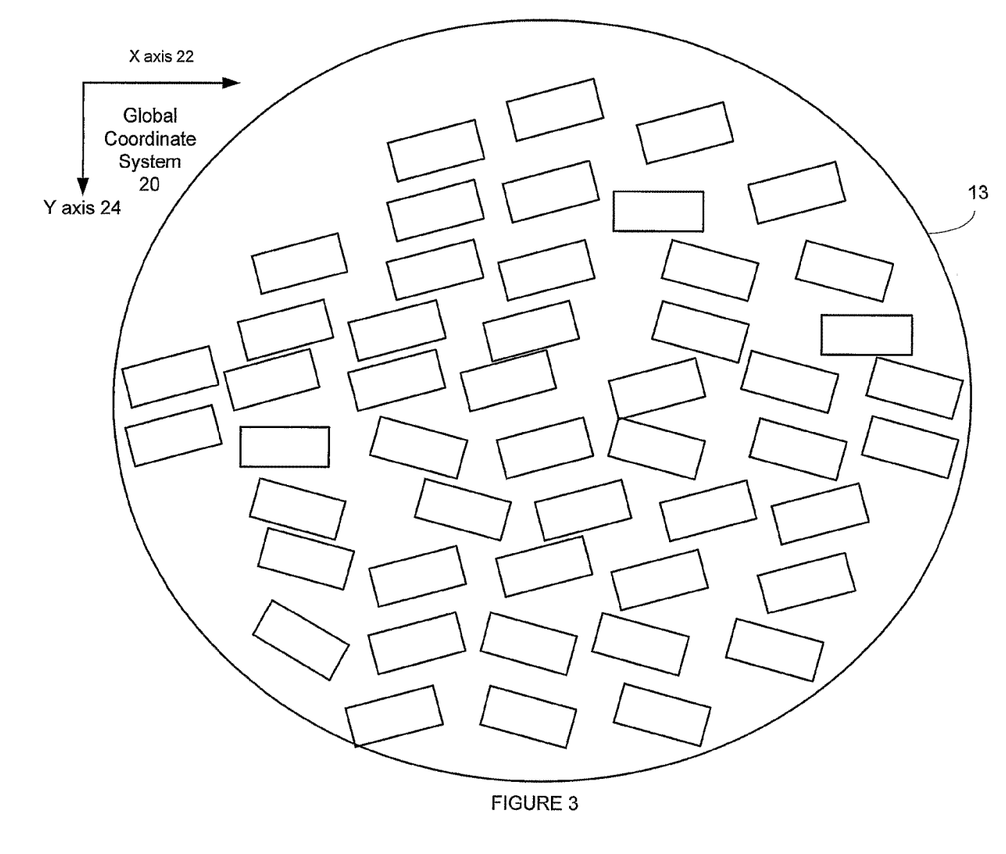
FIG. 3 illustrates a prior art diced wafer.

FIG. 3 illustrates an exemplary diced wafer 13. The dice (collectively denoted 14) of diced wafer 13 are not parallel to each other and diced wafer 13 is also misaligned (rotated) in relation to global coordinate system 20. The latter rotation can result from angular misalignments as well as mechanical inaccuracies.

Wafers and diced wafers are inspected for defects. The inspection can involve comparing between a die and a reference die. The following patents, all being incorporated herein by reference, illustrate various wafer inspection devices and methods as well as registration and alignment methods: U.S. Pat. No. 5,610,102 of Gardopee et al., U.S. Pat. No. 6,021,380 of Fredriksen et al., U.S. Pat. No. 6,937,753 of O'Dell et al., and U.S. Pat. No. 6,324,298 of O'Dell et al., and U.S. Pat. No. 4,981,529 of Tsujita.

Various prior art diced wafer inspection methods included locating a unique feature, comparing its location to an expected location, changing the scanning pattern in response to the differences between the actual location to the expected location and continuing to the next expected location of the unique feature.

There is a need to provide an inspection system that can inspect diced wafers and a method for inspecting diced wafers.

SUMMARY OF THE INVENTION

A method for inspecting a diced wafer that comprises multiple dice, the method includes: acquiring multiple images of multiple portions of the diced wafer according to a predefined image acquisition scheme; locating multiple unique features within the multiple images; and assigning a die index to each die of the multiple dice and associating between the multiple dice and multiple reference dice in response to locations of the multiple unique features and to at least one expected die dimension.

An inspection system, the system includes: an image acquisition unit adapted to acquire multiple images, according to a predefined image acquisition scheme, of multiple portions of a diced wafer that comprises multiple dice; and a processor adapted to locate multiple unique features within the multiple images, assign a die index to each dice of the multiple dice; and associate between the multiple dice and multiple reference dice in response to locations of the multiple unique features, to at least one expected die.

BRIEF DESCRIPTION OF THE DRAWINGS

The present invention will be understood and appreciated more fully from the following detailed description taken in conjunction with the drawings in which.

DETAILED DESCRIPTION OF THE DRAWINGS

Various embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Conveniently, a diced wafer map is generated and a die index is associated with each die of the diced wafer. Multiple images are acquired conveniently according to a predefined image acquisition scheme that defines diced wafer scanning patterns. The method does not require stopping the scanning process in order to adjust the scanning pattern in response to differences between an actual location of a unique feature and the expected location of this feature.

In addition, the scanning pattern can start at any location of the diced wafer, and not necessarily start from a predefined location such as the upper left end of the diced wafer. A first die index can be assigned to a die that is located at various locations of the diced die.

According to an embodiment of the invention the predefined image acquisition scheme includes defining a certain scanning pattern that is not altered in response to detections of unique features or the associations of dice with dice indexes. Scanning patterns can include rater scan patterns but this is not necessarily so.

Figure 4:
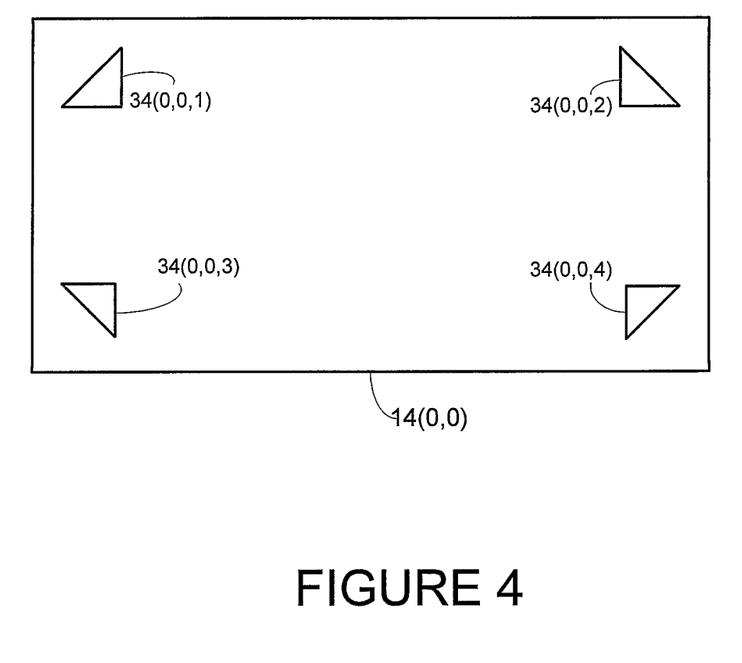
FIG. 4 illustrates a die that includes multiple unique features.

FIG. 4 illustrates a die 14(0,0) that includes four unique features 34(0,0,1)-34(0,0,4). These unique small features are not removed due to the dicing process. Once two or more unique features are identified the orientation of die 14(0,0) as well as its position can be determined.

Figure 5:
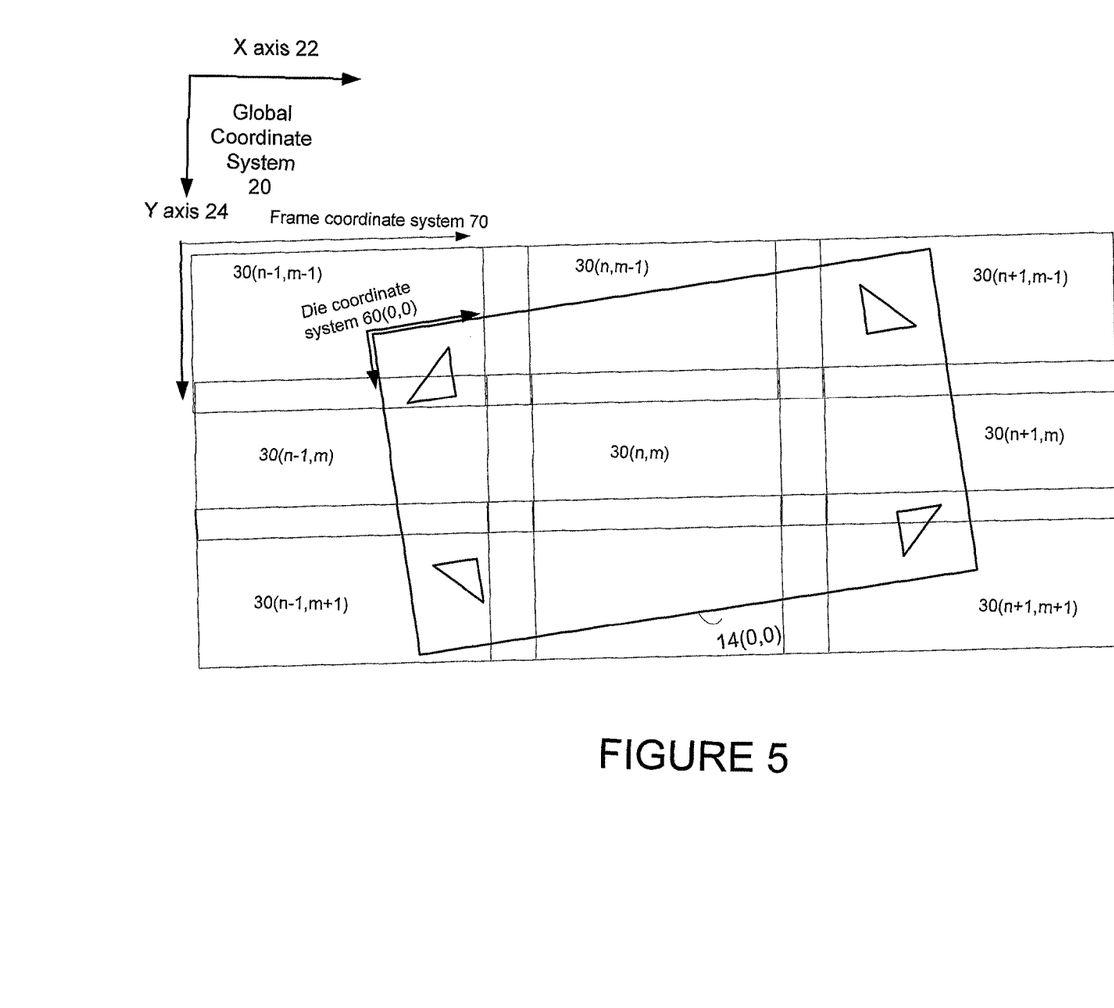
FIG. 5 illustrates multiple images, a die and three coordinate systems according to an embodiment of the invention.

FIG. 5 illustrates multiple images 30(n−1,m)-30(n+1, m+2), die 14(0,0) and three coordinate systems according to an embodiment of the invention.

Die 14(0,0) defines a die coordinate system 60(0,0). Each die of diced wafer 13 defines its own coordinate system. These die coordinate systems are usually not aligned with global coordinate system 20.

FIG. 5 also illustrates multiple images (also referred to as frames) that represent the images that are acquired by an image acquisition unit. These images are aligned with a frame coordinate system 70. Conveniently, the different die coordinate systems are not aligned with the frame coordinate system 70. Frame coordinate system 70 can be aligned with global coordinate system 20 but this is not necessarily so, as illustrated by FIG. 5. This misalignment can result from mechanical inaccuracies of the inspection system as well as from other reasons. Typically, the spatial relationship between global coordinate system 20 and frame coordinate system 70 can be determined during a calibration sequence of the inspection system.

FIG. 5 illustrates by set of 3×3 images 30(n−1,m−1)-30(n+1, m+1) that cover die 14(0,0) as well as its proximate vicinity. FIG. 5 illustrates that images 30(n−1,m−1) includes unique feature 34(0,0,1), image 30(n+1,m−1) includes unique feature 34(0,0,2), image 30(n−1, m+1) includes unique feature 34(0,0,3) and image 30(n+1, m+1) includes unique feature 34(0,0,4). Image (n−1, m) includes a part of unique feature 34(3,3,1) and image 30(n+1,m) includes a part of unique feature 34(0,0,4).

Figure 6:
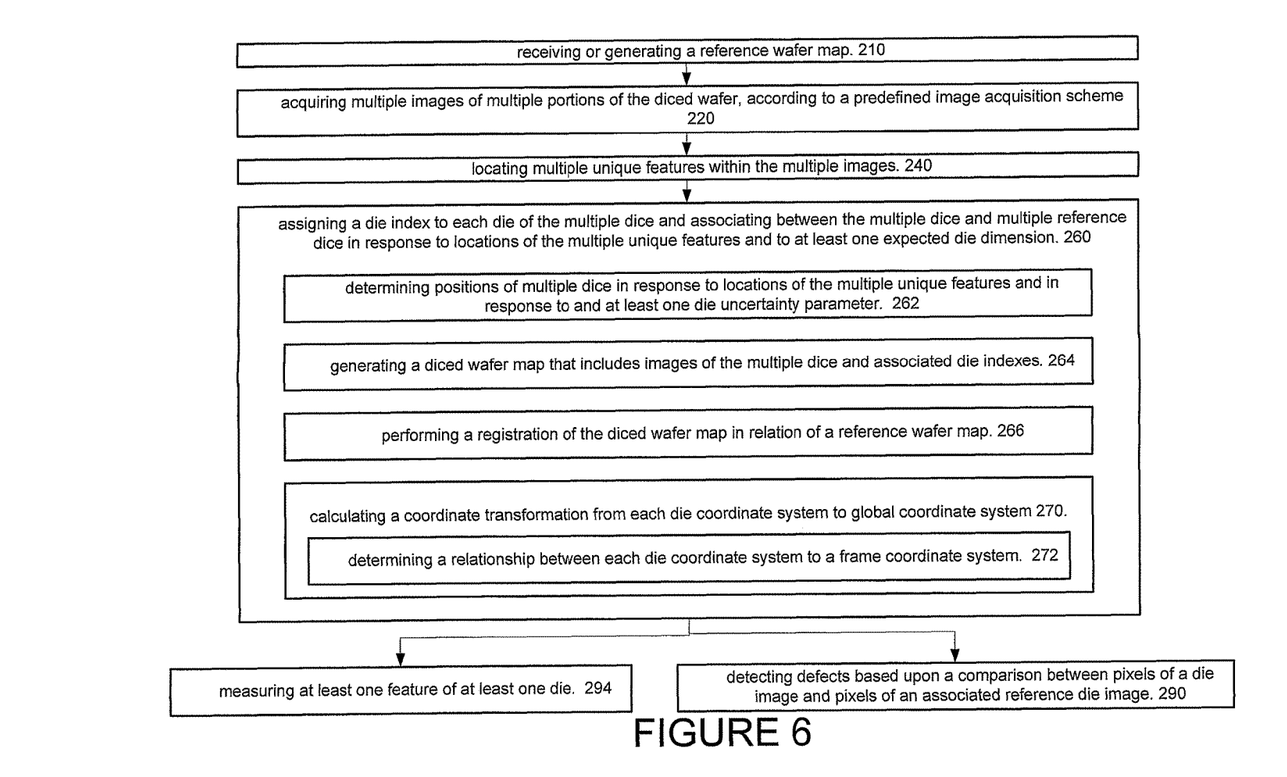
FIG. 6 illustrates a method for inspecting a wafer according to an embodiment of the invention.

FIG. 6 illustrates method 200 for inspecting a diced wafer, according to an embodiment of the invention.

Method 200 starts by stage 210 of receiving or generating a reference wafer map.

Stage 210 is followed by stage 220 of acquiring multiple images of multiple portions of the diced wafer according to a predefined image acquisition scheme.

Conveniently, stage 220 includes acquiring partially overlapping images.

Conveniently, stage 220 includes introducing a continuous mechanical translation between the diced wafer and an image acquisition unit. It is noted that the diced wafer can be illuminated by a continuous light source, by a pulsed light source, and an area illumination, by a spot light source, by applying bright field detection or dark field detection and the like.

Stage 220 is followed by stage 240 of locating multiple unique features within the multiple images.

Conveniently, stage 240 includes applying normalized correlation or geometric hashing. Geometric hashing is described in the following articles and patents, all being incorporated herein by reference: "Rehashing for Bayesian Geometric Hashing", M. Lifshits, I. Blayvas, R. Goldenberg and E. Rivlin, Proceedings of the $17^{th}$ international conference on pattern recognition (ICPR'04), "Geometric Hashing: An Overview, H. J. Wolfson and I. Rigoutsos, IEEE Computational Science & Engineering, 1997 IEEE, U.S. Pat. No. 6,941,016 of Wagman et al., U.S. Pat. No. 7,027,651 of Simon et al., and U.S. Pat. No. 6,993,192 of Silver.

Conveniently, stage 240 includes applying multiple image recognition techniques.

Stage 240 is followed by stage 260 of assigning a die index to each die of the multiple dice and associating between the multiple dice and multiple reference dice in response to locations of the multiple unique features and to at least one expected die dimension.

Conveniently, stage 260 includes stage 262 of determining positions of multiple dice in response to locations of the multiple unique features and in response to and at least one die uncertainty parameter. The at least one die uncertainty parameter can reflect the rotations, shifts and movements of a die during the sawing and expanding process.

Conveniently, stage 262 is followed by stage 264 of generating a diced wafer map that includes images of the multiple dice and associated die indices. Stage 264 can include generating a diced wafer map that includes positions of the multiple dice in the global coordinate system.

Conveniently, stage 264 is followed by stage 266 of performing a registration of the diced wafer map in relation of a reference wafer map.

Conveniently, each die is characterized by a die coordinate system and stage 262 is also followed by stage 270 of calculating a coordinate transformation from each die coordinate system to global coordinate system 20.

Conveniently, stage 270 includes stage 272 of determining a relationship between each die coordinate system to a frame coordinate system. The coordinate transformation is responsive to the determined relationship and to a relationship between the global coordinate system and the frame coordinate system. The relationship between the global coordinate system and the image acquisition system can be determined during an inspection system calibration session.

Conveniently, stages 240 and stage 220 partially overlap. Conveniently, stage 220 and 260 partially overlap. Accordingly, while certain images are acquired, unique features within previously acquired images can be located and even certain dice (of which images were previously acquired) can be associated with corresponding wafer dice and even be assigned a die index.

Conveniently, stage 240 of locating multiple unique features and stage 260 of assigning multiple die indexes include a sequence (such as sequence 300 illustrated in FIG. 7) of unique feature detection and die index assignment stages. Sequence 300 can start by locating a first unique feature, and assigning a first die index to a first dice that includes the unique feature. The sequence can continue by repetitively locating another unique feature that belongs to another die and assigning another die index to the other die. The relationship between the first and other die indexes is responsive to a spatial relationship between the first and other unique features. For example, the relationship between the die width or die length, (or X axis die pitch and Y axis die pitch) as well as the expected uncertainty associated with the dicing process can determine the die index assigned to the other die. If two dice are adjacent dice then their die indexes should differ by one.

Conveniently, stage 260 is followed by stage 290 of detecting defects based upon a comparison between pixels of a die image and pixels of an associated reference die image.

Conveniently, stage 260 is followed by stage 294 of measuring at least one feature of at least one die. The measurement can include analyzing images of the die and determining the length or width of a feature, in a pixel or sub-pixel accuracy.

Figure 7:
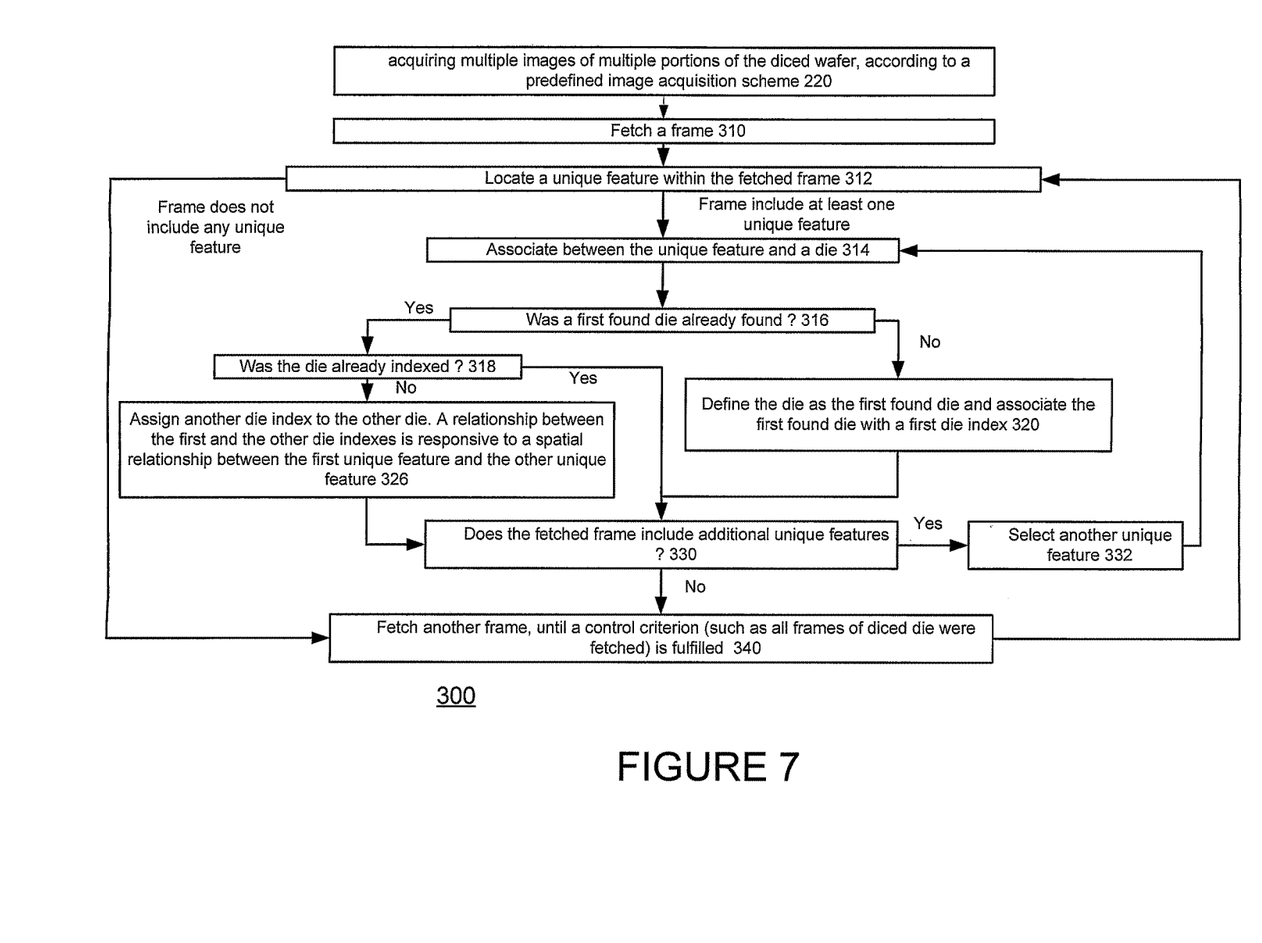
FIG. 7 illustrates a sequence of stages according to an embodiment of the invention.

FIG. 7 illustrates sequence 300 of stages according to an embodiment of the invention.

Sequence 300 is preceded by stage 220 of acquiring multiple images of multiple portions of the diced wafer according to a predefined image acquisition scheme. For example, referring to FIG. 5, it is assumed that image 30(n−1, m−1) is the first acquired image and that unique feature 34(0,0,1) is the first detected unique feature.

Sequence 300 starts by stage 310 of fetching a frame. Stage 310 is followed by stage 312 of locating one or more unique features within the fetched frame. If no unique feature is found then stage 312 is followed by stage 340 of fetching another frame that was not previously fetched, until a fetching criterion is found (for example—all frames of the diced die were fetched). Stages 340 and 312 are followed by stage 314.

Stage 314 includes associating between a unique feature and a die.

Stage 314 is followed by stage 316 of determining if a first found die was already found (was already indexed). If the answer is negative (meaning that the unique feature is the first found unique feature and it belongs to the first found die) then stage 316 is followed by stage 320 of defining the die as the first found die and associating it with a first die index such as index (0,0). Stage 320 is followed by stage 330.

If the answer is positive (the first found die and optionally other die were already detected) then stage 316 is followed by stage 318 of determining whether the currently associated die was indexed. If the answer is positive then stage 318 is followed by stage 330. If the answer is negative stage 318 is followed by stage 326 of assigning another die index to another (the other) die. The relationship between the first die and this other die is responsive to the spatial relationship between the first unique feature and the other unique feature (found during the latest iteration of stage 312). The assignment can be responsive to die pitch and uncertainties associated with the dicing and expanding processes (such as rotation, sheer, shift and the like). Stage 326 is followed by stage 330.

Stage 330 follows stages 318, 326 and 320. It includes determining whether the fetched frame include additional unique features. If the answer is positive stage 326 is followed by stage 332 of selecting another unique feature and then jumping to stage 314. Else, stage 330 is followed by stage 340

Figure 8:
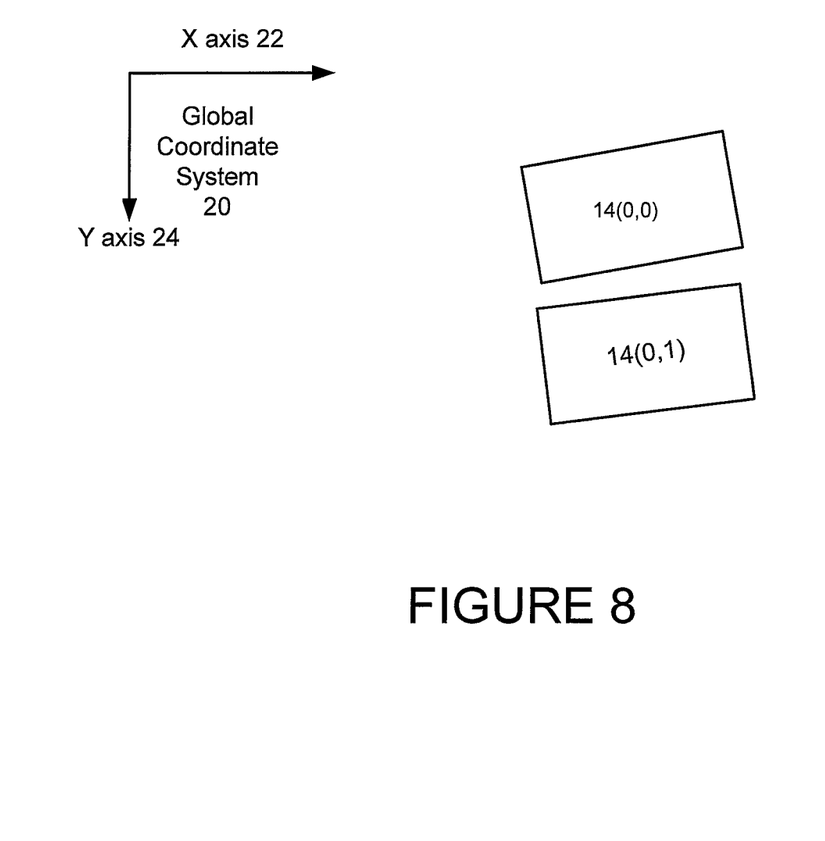
FIG. 8 illustrates a first found die and a second found fie according to an embodiment of the invention.
Figure 9:
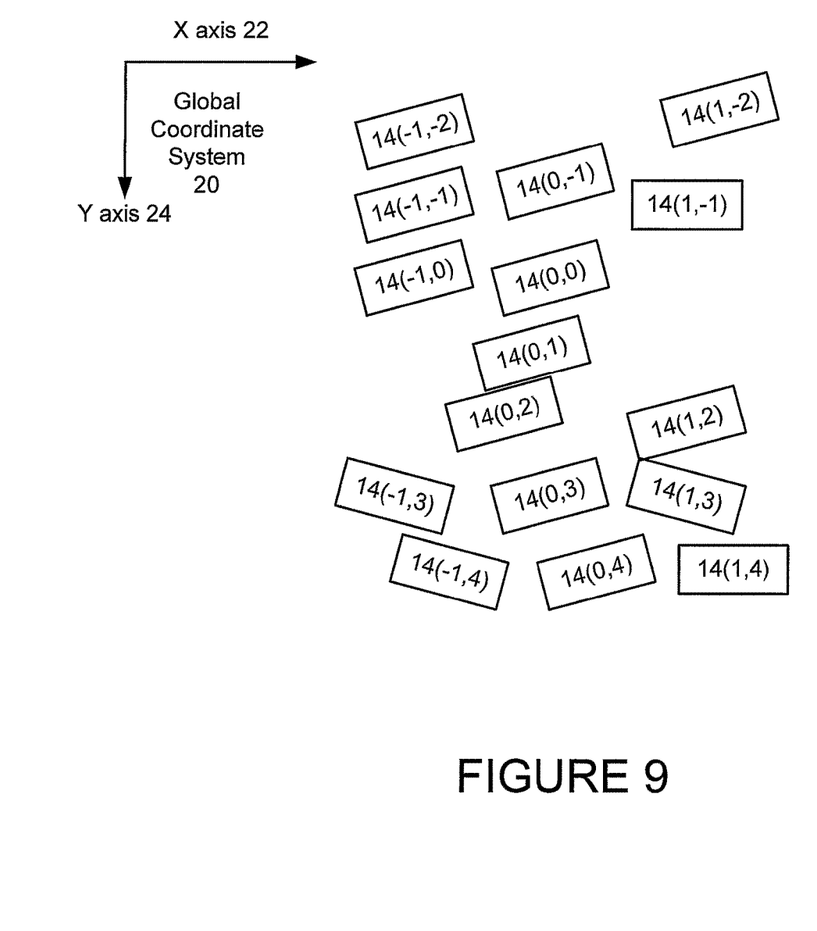
FIG. 9 illustrates multiple found dice according to an embodiment of the invention.

Referring, for example to the example set forth in FIG. 8, the first found die is denoted 14(0,0) and the adjacent die below the first found die is associated with index (0,1) Referring, for example to the example set forth in FIG. 9, the first found die is associated with index (0,0) while additional dice are associated with indexes that range between (−1,−2) and (1,4).

After images of the whole diced wafer are processed a diced wafer map is generated.

Each die within the diced wafer map can then be associated with a corresponding die of the reference wafer map. After the diced wafer map is generated an imaginary warped grid that connects the centers of dice of the diced wafer can be defined.

It is noted that after all dice in the diced wafer are assigned a die index these die indexes can be replaced by dice indexes that indicate (or are related to) the dice indexes in the pre-diced index.

Figure 10:
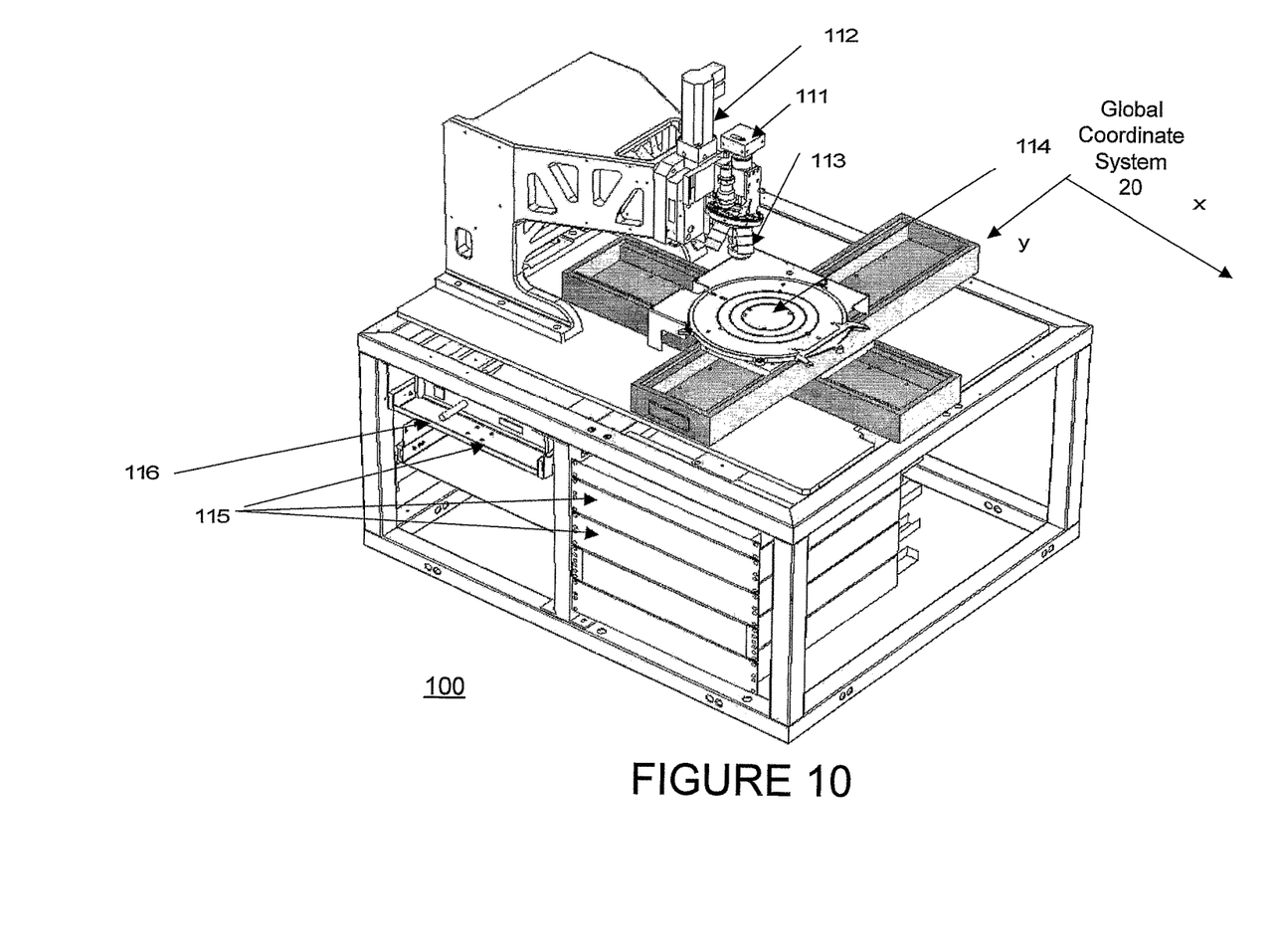
FIG. 10 illustrates a system, according to an embodiment of the invention.

FIG. 10 illustrate system 100 according to an embodiment of the invention. System 100 includes image acquisition unit 111, processor 115, illuminator 112, optics 113, a mechanical stage such as X-Y table 114 and storage unit 116.

System 100 can define or receive a predefined image acquisition scheme and accordingly scan the diced wafer while acquiring images.

X-Y table 114 is adapted to introduce a continuous mechanical translation between the diced wafer and the image acquisition unit.

Image acquisition unit 111 can include one or more detectors that can acquire an image of an area illuminated by illuminator 112. Optics 13 may serve the illumination of a diced wafer (placed on X-Y table 114) as well as serve for collecting light and directing it towards image acquisition unit 111. Storage unit 116 stored acquired images and is accessible by processor 115. It is noted that the detection signals from image acquisition unit 111 can be processed by processor 115 in order to provide images (or frames).

The diced wafer can be illuminated by overlapping strobes of light that forming overlapping images of frames.

The motion of X-Y table 114 is managed electronically by high precision control system, this enables to correlate the exact location of each pixel in the scanned object (image) in relation to global coordinate system 20.

Conveniently, image acquisition unit 112 is adapted to acquire multiple images of multiple portions of a diced wafer that include multiple dice while processor 115 is adapted to: (i) locate multiple unique features within the multiple images, (ii) assign a die index to each dice of the multiple dice; and (iii) associate between the multiple dice and multiple reference dice in response to locations of the multiple unique features, to at least one expected die.

Conveniently processor 115 is adapted to perform at least one of the following operations, or a combination thereof: (i) determine positions of multiple dice in response to locations of the multiple unique features and in response to at least one die uncertainty parameter; (ii) generate a diced wafer map that includes images of the multiple dice and associated die indexes; (iii) calculate a coordinate transformation from each die coordinate system to a global coordinate system; (iv) determine a relationship between each die coordinate system to a frame coordinate system; wherein the coordinate transformation is responsive to the determined relationship and to a relationship between the global coordinate system and the frame coordinate system; (v) locate a first unique feature and assign a first die index to a first dice that includes the unique feature; (vi) locate another unique feature that belongs to another dice and assign another die index to the other dice; wherein a relationship between the first and the other die indexes is responsive to a spatial relationship between the first and other unique features; (vii) perform a registration of the diced wafer map in relation of a reference wafer map; (viii) detect defects based upon a comparison between pixels of a dice image and pixels of an associated reference dice image; (ix) locate at least one unique feature while the image acquisition unit acquires at least one image; (x) associate between at least one die and at least one reference die while the image acquisition unit acquires at least one image; (xi) locate at least one unique feature by applying normalized correlation or geometric hashing; (xii) locate at least one unique feature by applying multiple image recognition techniques; or (xiii) measure at least one feature of at least one die.

It is noted that memory unit 116 can also store images of the reference dice as well as information (such as die index) relating to the acquired images of the dice of the diced wafer. It can store a reference wafer map, and alternatively or additionally the diced wafer map.

Image acquisition unit 111 can include one or more line sensors, point sensors, two dimension sensor arrays and the like. Illuminator 112 can include a laser source a lamp, can provide light pulses or continuous illumination, can illuminate a spot or illuminate an area. Illuminator 112 is illustrated as bright field illuminator but system 100 can apply, additionally or alternatively, dark filed illumination.

Processor 115 can also control the operation of the various components of system 100 but this is not necessarily so and system 100 can include one or other controllers that control the operation of system 100.

Conveniently, processor 115 can include multiple components that can operate in parallel in order to increase the processing speed of system 100. These components can perform the same function or different functions.

Conveniently, storage unit 116 may include one or multiple storage components that be accessed serially or in a parallel manner, for speeding to processing speed of system 100. Different storage unit components can store different type of information or the same type of information.

Although the invention has been described in conjunction with specific embodiments thereof, it is evident that many alternatives, modifications and variations will be apparent to those skilled in the art, accordingly, it is intended to embrace all such alternatives, modifications and variations that fall within the spirit and broad scope of the appended claims.

We claim:

1. A method for inspecting a diced wafer that comprises multiple dice, the method comprises;
    acquiring, by one or more detectors of an image acquisition unit of an inspection system, multiple images of multiple portions of the diced wafer according to a predefined image acquisition scheme; wherein the multiple portions comprise multiple dice; wherein the acquiring of the multiple images comprises illuminating, by an illuminator, the multiple portions of the diced wafer; wherein the diced wafer is generated by (a) dicing a pre-diced wafer to separate between different dies of the wafer, and (b) preforming an expanding process that involves pulling away the different dice from each other;
    locating multiple unique features within the multiple images;
    determining, by a processor of the inspection system, positions of the multiple dice in response to locations of the multiple unique features;
    and
    assigning a die index to each die of the multiple dice in response to uncertainties associated with the dicing and expanding processes;
    associating between the multiple dice and multiple reference dice in response to locations of the multiple unique features and to at least one expected die dimension; and
    performing at least one out of (i) measuring, by the processor, at least one feature of at least one die, and (ii) detecting, by the processor, defects based upon a comparison between pixels of a die image and pixels of an associated reference die image.

2. The method according to claim 1 wherein the associating comprises determining positions of multiple dice in response to locations of the multiple unique features and in response to and at least one die uncertainty parameter that reflects rotations, shifts and movement of a die during the dicing and the expanding process.

3. The method according to claim 1 wherein the associating comprises generating a diced wafer map that comprises images of the multiple dice and associated die indexes.

4. The method according to claim 1 wherein each die is characterized by a die coordinate system and wherein the method comprises calculating a coordinate transformation from each die coordinate system to a global coordinate system.

5. The method according to claim 4 wherein the calculating comprises determining a relationship between each die coordinate system to a frame coordinate system; wherein the multiple images are aligned with the frame coordinate system; wherein the coordinate transformation is responsive to the determined relationship and to a relationship between the global coordinate system and the frame coordinate system.

6. The method according to claim 1 wherein the acquiring comprises introducing a continuous mechanical translation between the diced wafer and an image acquisition unit.

7. The method according to claim 1 wherein the locating comprises locating a first unique feature and the associating comprises assigning a first die index to a first dice that comprises the unique feature.

8. The method according to claim 7 wherein the locating comprising locating another unique feature that belongs to another dice and assigning another die index to the other dice; wherein a relationship between the first and the other die indexes is responsive to a spatial relationship between the first and other unique features.

9. The method according to claim 1 further comprising generating a reference wafer map.

10. The method according to claim 1 wherein the associating comprises performing a registration of the diced wafer map in relation of a reference wafer map.

11. The method according to claim 1 further comprising detecting defects based upon the comparison between pixels of the die image and pixels of the associated reference die image.

12. The method according to claim 1 wherein the stage of locating multiple unique features at least partially overlaps the stage of acquiring multiple images.

13. The method according to claim 1 wherein the stage of associating between the multiple dice and the multiple reference dice at least partially overlaps the stage of acquiring multiple images.

14. The method according to claim 1 wherein the stage of locating comprises applying normalized correlation or geometric hashing.

15. The method according to claim 1 wherein the stage of locating comprises applying multiple image recognition techniques.

16. The method according to claim 1 wherein the stage of associating is followed by measuring the at least one feature of the at least one die.

17. The method according to claim 1 wherein the acquiring comprises acquiring partially overlapping images.

18. An inspection system, the system comprises:
an illuminator that is adapted to illuminate multiple portions of a diced wafer;
an image acquisition unit that comprises one or more detectors that are adapted to acquire multiple images, according to a predefined image acquisition scheme, of the multiple portions of the diced wafer that comprises multiple dice;
wherein the multiple portions comprise multiple dice; wherein the diced wafer is generated by (a) dicing a pre-diced wafer to separate between different dies of the wafer, and (b) preforming an expanding process that involves pulling away the different dice from each other; and
a processor adapted to (a) locate multiple unique features within the multiple images, (b) determine positions of the multiple dice in response to locations of the multiple unique features; (c) assign a die index to each dice of the multiple dice in response to uncertainties associated with the dicing and expanding processes; associate between the multiple dice and multiple reference dice in response to locations of the multiple unique features, to at least one expected die; and perform at least one out of (i) measure at least one feature of at least one die, and (ii) detect defects based upon a comparison between pixels of a die image and pixels of an associated reference die image.

19. The system according to claim 18 wherein the processor is adapted to determine positions of multiple dice in response to locations of the multiple unique features and in response to at least one die uncertainty parameter that reflects rotations, shifts and movement of a die during the dicing and the expanding process.

20. The system according to claim 18 wherein the processor is adapted to generate a diced wafer map that comprises images of the multiple dice and associated die indexes.

21. The system according to claim 18 wherein each die is characterized by a die coordinate system and wherein the processor is adapted to calculate a coordinate transformation from each die coordinate system to a global coordinate system.

22. The system according to claim 21 wherein the processor is adapted to determine a relationship between each die coordinate system to a frame coordinate system; wherein the multiple images are aligned with the frame coordinate system; wherein the coordinate transformation is responsive to the determined relationship and to a relationship between the global coordinate system and the frame coordinate system.

23. The system according to claim 18 further comprising a mechanical stage adapted to introduce a continuous mechanical translation between the diced wafer and the image acquisition unit.

24. The system according to claim 18 wherein the processor is adapted to locate a first unique feature and assign a first die index to a first dice that comprises the unique feature.

25. The system according to claim 24 wherein the processor is adapted to locate another unique feature that belongs to another dice and assign another die index to the other dice; wherein a relationship between the first and the other die indexes is responsive to a spatial relationship between the first and the other unique features.

26. The system according to claim 18 wherein the system comprises a storage unit adapted to store a reference wafer map.

27. The system according to claim 18 wherein the processor is adapted to perform a registration of the diced wafer map in relation of a reference wafer map.

28. The system according to claim 18 the processor is adapted to detect defects based upon a the comparison between pixels of a the die image and pixels of an the associated reference die image.

29. The system according to claim 18 wherein the processor is adapted to locate at least one unique feature while the image acquisition unit acquires at least one image.

30. The system according to claim 18 wherein the processor is adapted to associate between at least one die and at least one reference die while the image acquisition unit acquires at least one image.

31. The system according to claim 18 wherein the processor is adapted to locate at least one unique feature by applying normalized correlation or geometric hashing.

32. The system according to claim 18 wherein the processor is adapted to locate at least one unique feature by applying multiple image recognition techniques.

33. The system according to claim 18 wherein the processor is adapted to measure the at least one feature of the at least one die.

34. The system according to claim 18 wherein the image acquisition unit is adapted to acquire partially overlapping images.

35. The system according to claim 18 wherein the processor is adapted to replace the die indexes by dice indexes that are related to dice indexes in the pre-diced wafer.

36. The method according to claim 1 comprising replacing the die indexes by dice indexes that are related to dice indexes in the pre-diced wafer.

* * * * *